United States Patent [19]
Waldron

[11] Patent Number: 5,668,298
[45] Date of Patent: Sep. 16, 1997

[54] SELECTABLE MARKER FOR DEVELOPMENT OF VECTORS AND TRANSFORMATION SYSTEMS IN PLANTS

[75] Inventor: Clive Waldron, Indianapolis, Ind.

[73] Assignee: Eli Lilly and Company, Indianapolis, Ind.

[21] Appl. No.: 485,572

[22] Filed: Jun. 7, 1995

Related U.S. Application Data

[63] Continuation of Ser. No. 586,317, Sep. 19, 1990, which is a continuation of Ser. No. 169,560, Mar. 17, 1988, abandoned, which is a continuation of Ser. No. 685,824, Dec. 24, 1984, abandoned.

[51] Int. Cl.$^6$ .............................. A01H 5/00; A01H 5/10; C12N 15/31; C12N 15/84; C12N 5/04
[52] U.S. Cl. .......................... 800/205; 800/250; 800/255; 536/23.2; 536/23.4; 536/23.7; 435/69.1; 435/69.7; 435/70.1; 435/172.3; 435/194; 435/252.2; 435/320.1; 435/418
[58] Field of Search .............................. 435/172.3, 320.1, 435/69.1, 70.1, 240.4, 194, 252.2, 69.7; 536/23.2, 23.4, 23.7; 800/205, 250, 255

[56] References Cited

U.S. PATENT DOCUMENTS

| | | | |
|---|---|---|---|
| 4,536,475 | 8/1985 | Anderson | 435/172.3 |
| 4,727,028 | 2/1988 | Santerre et al. | 435/240.2 |
| 4,960,704 | 10/1990 | Ingolia et al. | 435/252.3 |

FOREIGN PATENT DOCUMENTS

| | | | |
|---|---|---|---|
| 74947/87 | 6/1987 | Australia | 435/172.3 |
| 80893/87 | 11/1987 | Australia | 435/172.3 |
| 0140556 | 9/1984 | European Pat. Off. | 435/172.3 |
| 0140556 | 5/1985 | European Pat. Off. | |
| 0298478 | 4/1988 | European Pat. Off. | 435/172.3 |
| 2100738 | 1/1983 | United Kingdom | 435/172.3 |
| WO 84/02913 | 8/1984 | WIPO | |
| PCT/US85/02488 | 6/1986 | WIPO | |

OTHER PUBLICATIONS

Reddy et al., (1988) Indian. J. Exp. Biol. 26:567–582.
Southern and Berg, (1981), Appl. Genet. 1:(4):327–341.
Foster, (1983) Microbiol. Rev. 47:361–409.
Bagdasarian et al., (1981), Gene 16:234–247.
Bevan et al., (1983), Nature 304:184–187.

(List continued on next page.)

*Primary Examiner*—David T. Fox
*Attorney, Agent, or Firm*—Pennie & Edmonds, LLP

[57] ABSTRACT

The present invention discloses functional and selectable micro-Ti plasmids. The hygromycin phosphotransferase (aphIV) gene from *Escherichia coli* was inserted between the 5' promoter and associated amino terminal region-encoding sequence of an octopine synthetase gene and the 3' terminator signal sequence of a nopaline synthetase gene. These constructs were assembled between T-DNA border fragments in a broad-host-range vector and used to create antibiotic-resistant plant cells.

27 Claims, 3 Drawing Sheets

RESTRICTION SITE AND FUNCTION MAP OF PLASMID pCEL40
(8.45 kb)

OTHER PUBLICATIONS

Bevan, (1984), "Binary Agrobacterium Vectors for Plant Transformation", Nucl. Acids Res. 12:8711–8721.
DeBlock et al., (1984), EMBO Journal 3:1681–1689.
deFramond et al., (1983), Biotechnology, May issue, pp. 262–269.
deFramond et al., (1983), Miami Winter Symp. 20:159–170.
DeGreve et al., (1983), J. Mol. Appl. Genet. 1:499–511.
Depicker et al., (1982), J. Mol. Appl. Genet. 1:561–573.
Fraley et al., (1983), Proc. Natl. Acad. Sci. 80:4803–4807.
Gonzalez et al., (1978), "Studies on the Mode of Action of Hygromycin B, an Inhibitor of Translocation in Eukaryotes", Biochim. & Biophys. Acta. 521:459–469.
Goodman et al., (1987) Science 236:48–54.
Herrera–Estrella et al., (1983), "Chimeric Genes as Dominant Selectable Markers in Plant Cells", EMBO Journal 2:987–995.
Herrera–Estrella et al., (1983), Nature 303:209–213.
Hoekema et al., (1983), Nature 303:179–180.
Hooykaas–Van Slogteren et al., (1984), Nature 311:763–764.
Joos et al., (1983), EMBO Journal 2:2151–2160.
Kaster et al., (1983), "Analysis of a Bacterial Hygromycin B Resistance Gene by Transcriptional and Translational Fusions and by DNA Sequencing", Nuc. Acids Res. 11:6895–6911.
Kaster et al., (1984), "Hygromycin B Resistance as Dominant Selectable Marker in Yeast", Curr. Genet. 8:353–358.
Murai et al., (1983), Science 222:476–482.
Paszkowski et al., (1984), EMBO Journal 3:2717–2722.
Rao et al., (1983), "Genetic and Enzymatic Basis of Hygromycin B Resistance in *Escherichia coli*", Antimicrob. Ag. and Chemother. 24:689–695.
Zambryski et al., (1983), EMBO Journal 2:2143–2150.

RESTRICTION SITE AND FUNCTION MAP OF
PLASMID pCEL30
(7.15 kb)

FIG. 1

RESTRICTION SITE AND FUNCTION MAP OF
PLASMID pCEL40
(8.45 kb)

FIG.2

RESTRICTION SITE AND FUNCTION MAP OF
PLASMID pCEL44
(17.5 kb)

SELECTABLE MARKER FOR DEVELOPMENT OF VECTORS AND TRANSFORMATION SYSTEMS IN PLANTS

This application is a continuation of application Ser. No. 07/586,317 filed Sep. 19, 1990, currently pending, which is a continuation of application Ser. No. 07/169,560 filed Mar. 17, 1988, abandoned, which is a continuation of application Ser. No. 06/685,824 filed Dec. 24, 1984, abandoned.

BACKGROUND OF THE INVENTION

Crown gall formation on dicotyledonous plants by *Agrobacterium tumefaciens* is the result of the transfer and covalent integration of a small segment called transfer DNA (T-DNA) of a tumor-inducing (Ti) plasmid into the chromosomal DNA of plant cells. The transferred T-DNA is expressed in plant cells and codes for several polyadenylated transcripts. Some of the transcripts are known to be responsible for opine synthesis and for tumor growth; these latter transcripts are encoded by oncogenes. None of these transcripts have been found to be essential for T-DNA transfer. The transfer mechanism is thought to involve repeated nucleotide sequences present near the T-DNA borders. As long as these borders are present, a foreign gene can be inserted into the T-DNA of a Ti plasmid and thus engineered into the genome of a tumor cell or regenerated plant.

In addition to the T-DNA sequences, it is generally believed that another set of Ti plasmid genes, located outside the T-DNA, termed the VIR (virulence) region, play a role in the mobilization of the T-DNA from the bacterium to the plant cell. Heretofore, the presence of the crown gall (tumor) on plants infected by an Agrobacterium carrying both the T-DNA and VIR regions has been the primary means of identifying transformed plant cells. This means of identification has limited commercial utility however, because whole plants can not be regenerated from crown galls containing functional oncogenes. Thus, it would be advantageous to develop a way of introducing and expressing foreign genes in plant cells without relying on tumor genes for the selection and identification of transformed plant cells.

Presently, a variety of methods to introduce DNA into plant cells are available with varying degrees of success. These methods include the use of liposomes to encapsulate one or more DNA molecules, the contacting of plant cells with DNA (which is complexed with either polycationic substances or calcium phosphate) and protoplast fusion techniques. Currently, the preferred technique involves the utilization of Ti plasmids from Agrobacterium cells to transfer a desired gene into a plant cell. Recently, researchers at Monsanto Company have demonstrated the availability of a co-integrant Ti plasmid for use in a method for transforming plant cells. (See, Fraley and Rogers, PCT Application WO84/0219). In addition, a Ti binary vector system, developed by Hoekema et al., 1983, *Nature* 303:179, is known in the art.

The aforementioned T-DNA region from the Ti plasmid is available for the insertion of a desired gene which is under the control of a functional plant expression mechanism. Such chimeric genes are known in the art to express both plant- and bacterial-derived polypeptides. Prior to the present invention, a chimeric protein, that is, a heterologous gene which is fused to a portion or whole of a structural plant gene, had never been expressed in a plant cell. The present vector constructions provide for the production of such a chimeric protein and thus contributes to the continuing development of plant transformation systems.

As demonstrated for bacterial and mammalian cells, one of the primary steps in the development of efficient transformation systems is the construction of dominant selectable markers. Such markers allow cells that have acquired new genes via transformation to be selected and identified easily. The present invention provides novel expression vectors which demonstrate that the aminocyclitol antibiotic hygromycin B can be the basis of such a selection scheme for transformed plant cells.

The present invention further provides a method of selecting transformed plant cells from a background of nontransformed cells. The method allows one to add non-selectable DNA to the present vectors, transform plant cells with the modified vectors and select hygromycin resistant transformants containing this otherwise non-selectable DNA. Since transformation is a very low frequency event, such a functional test is a practical necessity for determining which cell(s), of among millions of cells, has acquired the transforming DNA.

For purposes of the present invention, as disclosed and claimed herein, the following terms are defined below.

Recombinant DNA Cloning Vector—any autonomously replicating agent, including but not limited to plasmids, comprising a DNA molecule to which one or more additional DNA segments can or have been added.

Recombinant DNA Expression Vector—any recombinant DNA cloning vector into which one or more transcriptional and translational activating sequence(s) have been incorporated.

Promoter—the site on the DNA molecule to which RNA polymerase attaches and at which transcription is initiated.

Amino terminal region-encoding sequence—the region of DNA at which translation of mRNA into a polypeptide is initiated and a portion of the 5' end of the resulting polypeptide is produced.

Chimeric protein—a recoverable heterologous polypeptide which is synthesized from a gene containing a promoter and a portion of a homologous coding region.

Border Sequence—DNA sequence which contains the ends of the T-DNA.

Broad-host-range replicon—a DNA molecule capable of being transferred and maintained in many different bacterial cells.

Conjugation—the process whereby DNA is transferred from bacteria of one type to another type during cell-to-cell contact.

Crown Gall—a plant tumor caused by *Agrobacterium tumefaciens*.

Ti plasmid—a large Agrobacterium plasmid which confers the ability to induce tumors and promotes bacterial conjugation.

Micro-Ti Plasmid—a plasmid capable of replication in Agrobacteria and containing DNA flanked by T-DNA borders.

Non-oncogenic Strain—a strain of *Agrobacterium tumefaciens* which is unable to induce crown gall but retains the vir functions.

Transformations—the introduction of DNA into a recipient host cell that changes the genotype and results in a phenotypic change in the recipient cell.

SUMMARY OF THE INVENTION

In accordance with this invention, functional and selectable micro-Ti plasmids are disclosed. The hygromycin phosphotransferase (aphIV) gene from *Escherichia coli* was inserted between the 5' promoter and associated amino terminal region-encoding sequence of an octopine synthetase gene and the 3' terminator sequence of a nopaline synthetase gene. These constructs were assembled between T-DNA border fragments in a broad-host-range vector to form micro-Ti plasmids of the present invention.

The invention further provides a method for selecting a hygromycin-resistant recombinant-DNA containing plant cell. The method comprises:

a) conjugating a recombinant DNA expression vector of the present invention into an *Agrobacterium tumefaciens* strain;

b) inoculating a hygromycin-sensitive plant cell with said *Agrobacterium tumefaciens* containing the expression vector; and c) selecting cells transformed by said expression vector under hygromycin resistance selective conditions.

DESCRIPTION OF THE INVENTION

The present invention discloses a recombinant DNA expression vector which is functional and selectable in plants comprising:

1) a transcription unit, flanked by transfer-DNA border sequences, which comprises a promoter and associated amino terminal region-encoding sequence and a terminator signal sequence, wherein said sequences are derived from one or more genes which are naturally expressed in a plant cell;

2) an antibiotic resistance gene encoding sequence located between said promoter and associated amino terminal region-encoding sequence and said terminator sequence; and 3) a DNA fragment containing a replicon that is functional in Agrobacterium.

Figure 1:
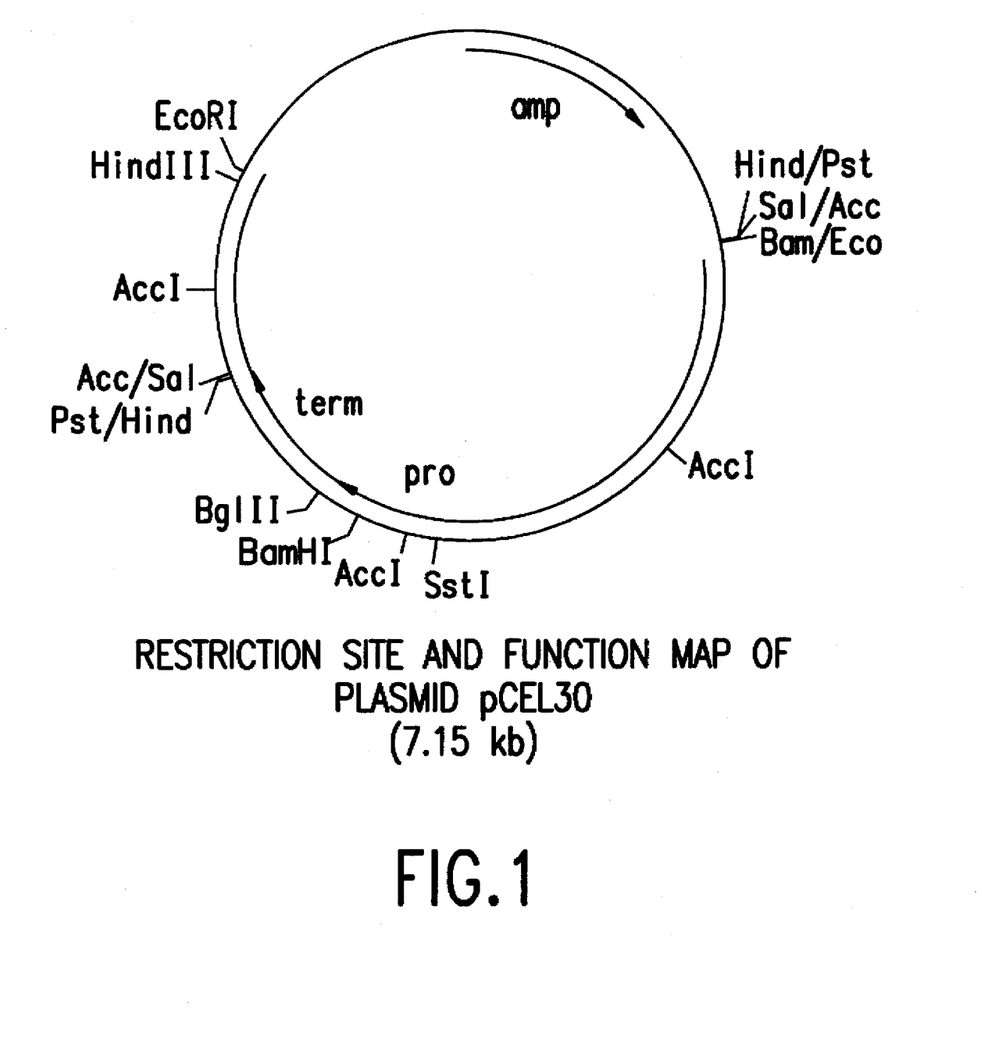
FIG. 1 shows the restriction site and function map of plasmid pCEL30.
Figure 2:
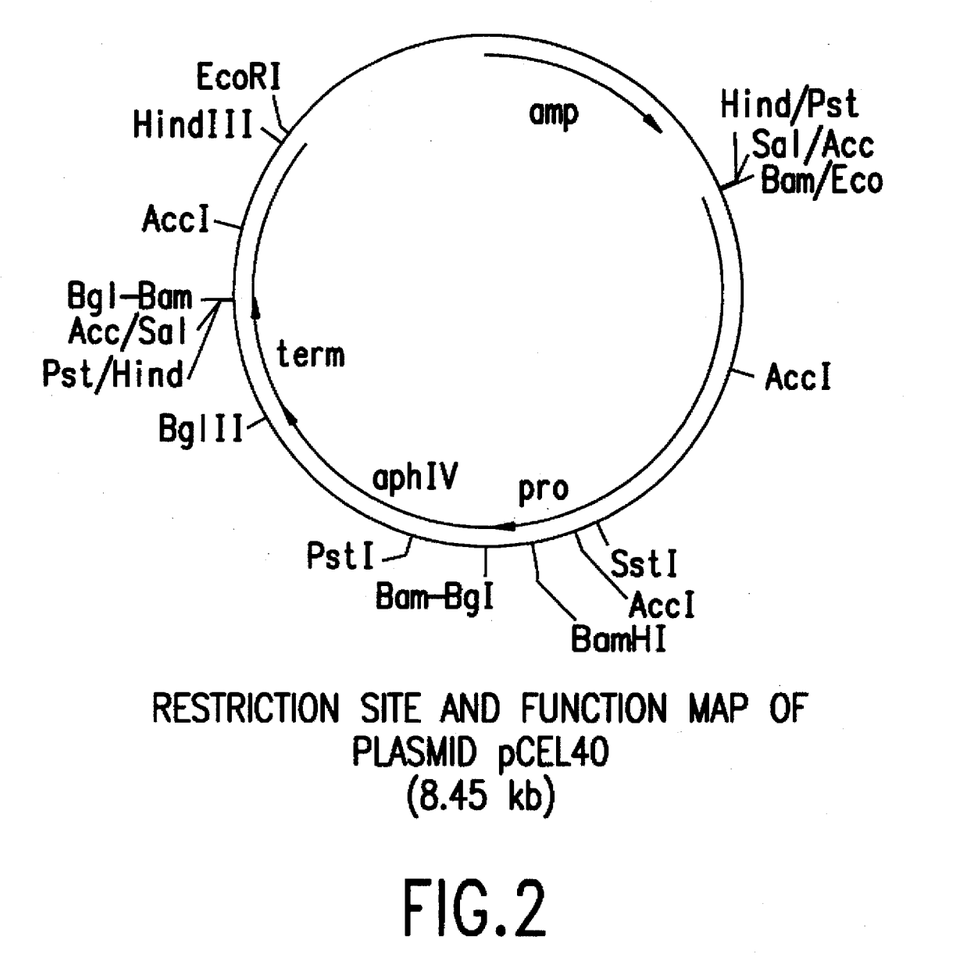
FIG. 2 shows the restriction site and function map of plasmid pCEL40.

In accordance with the invention, an ~1.3 kb BamHI-BglII fragment coding for hygromycin phosphotransferase was introduced, in both orientations, into a unique BglII restriction site of the intermediary cloning vector, plasmid pCEL30. Plasmid pCEL30 carries the promoter transcription signal and sequences coding for the first 11 amino acids of the ocs gene. The introduction of the hygromycin phosphotransferase (aphIV) encoding gene was engineered to maintain the reading frame of the octopine synthetase (ocs) coding region. Thus, the aphIV gene was subcloned into the BglII site of pCEL30, resulting—because of the specific sequences involved—in the generation of a BglII-BamHI fusion near the initiation codon of ocs. The resulting vector, plasmid pCEL40, encodes an ocs-aphIV fusion protein. When the aphIV gene was inserted in the opposite orientation, hygromycin phosphotransferase was not produced. A restriction site and function map of plasmids pCEL30 and pCEL40 is presented in FIGS. 1 and 2 of the accompanying drawings.

Plasmid pCEL30 can be conventionally isolated from *Escherichia coli* K12 RR1ΔM15/pCEL30, a strain deposited and made part of The Northern Regional Research Laboratory, Peoria, Ill. 61604. Plasmid pOW20, a source of the hygromycin phosphotransferase gene, is also deposited with the NRRL and can be readily isolated from *E. coli* JA221/pOW20. Both strains are avilable to the public, as a preferred source and stock reservoir of the plasmids, under the accession numbers NRRL B-15915 and NRRL B-15838, respectively.

Since plasmid pCEL40 is not capable of replication in Agrobacterium, the micro T-DNA of plasmid pCEL40 was first transferred, as an EcoRI fragment, into a broad-host-range vector pKT210. This host vector is available from the Plasmid Reference Center, Stanford University, Palo Alto, Calif. 94305. The use of a specific host-range vector is not critical in the construction of the present plasmids. Other such useful vectors include, for example, pRK290 (Ditta et al., 1980, *Proc. Natl. Acad. Sci.* 77:7347–7351 and R772 (Hoekema et al., 1983, *Nature* 303:179–180). If properly assembled and inserted into a plant genome, a fusion protein will be expressed in the plant cell to create a desired polypeptide, such as a bacterial enzyme which confers antibiotic resistance upon the plant. Thus, the resulting micro-Ti plasmid pCEL44 is extremely useful because it contains a selectable and functional plant gene for hygromycin resistance. In conjunction with the presence of a selectable and functional plant gene, the unique construction of plasmid pCEL44 confers additional beneficial attributes for use in plant transformation systems. For example, the T-DNA border sequences assist in the transfer and covalent integration of the transcription unit of the present micro-Ti plasmid into the chromosomal DNA of plant cells; the Agrobacteria-functional replicon provides an efficient means of plasmid replication and eliminates a co-integration step used by others skilled in the art; and the unique SalI cloning site provides a convenient cleavage site for insertion of a gene of interest.

The above-illustrated vector confers hygromycin resistance to plant cells because of the presence of a functional phosphotransferase aphIV gene. Although the particular phosphotransferase gene inserted in the above vector is an ~1.3 kb BamHI-BglII restriction fragment, other known phosphotransferase aphIV genes can be substituted. Such genes include, but are not limited to, those disclosed by Rao et al., 1983, *Antimicrobial Agents and Chemotherapy* 24:689–695. In addition, a variety of different plasmid pOW20 restriction fragments that contain the hygromycin resistance-conferring gene can also be substituted provided that any of these restriction fragments are positioned such that the promoter region causes the transcription of the structural sequence. The phosphotransferase aphIV gene is encoded on the ~1.3 kb BamHI-BglII fragment of plasmid pOW20, therefore any restriction fragment containing the afore-mentioned ~1.3 kb BamHI-BglII fragment also confers the desired resistance to sensitive plant host cells. Skilled artisans will recognize that all the above genes and fragments are functionally equivalent and thus can be used and interchanged for purposes of the present invention.

Restriction fragments used to construct vectors illustrative of the present invention can be conventionally modified to facilitate ligation. For example, molecular linkers can be provided to a particular phosphotransferase aphIV-containing restriction fragment, to DNA comprising the replication functions of the vector, or to DNA comprising the promoter or terminator sequences. Thus, specific sites for subsequent ligation can be constructed conveniently. In addition, any of these DNA fragments can be modified by adding, eliminating or substituting certain nucleotides to alter characteristics and to provide or eliminate a variety of restriction sites for ligation of DNA. Those skilled in the art understand nucleotide chemistry and the genetic code and thus which nucleotides are interchangeable and which DNA modifications are desirable for a specific purpose.

The present invention also discloses a method for selecting a hygromycin-resistant recombinant DNA-containing plant cell, said method comprising:

1) conjugating the recombinant DNA expression vector of the present invention into an *Agrobacterium tumefaciens* strain;

2) inoculating a hygromycin-sensitive plant cell with said *Agrobacterium tumefaciens* containing the expression vector; and 3) selecting cells transformed by said expression vector under hygromycin resistance selective conditions.

In accordance with the method of the invention, micro-Ti plasmids, such as pCEL44, were conjugated into different strains of *Agrobacterium tumefaciens*. Triparental matings were conducted with *E. coli* K12 RR1ΔM15/pCEL44, an *E. coli* containing the helper plasmid pRK2013 (Ditta et al., supra) and *A. tumefaciens* LBA4013, a strain that contains a wild-type Ti plasmid, pTiAch5. For purposes of this invention, the use of a specific helper plasmid or of a specific strain of *A. tumefaciens* is not critical. In this regard, any of the helper plasmids described in Bagdasarian et al., 1981, Gene 16: 237–247 can be substituted for plasmid pRK2013, as the sole function of this kanamycin-resistant helper plasmid pRK2013 is to trans-complement the micro-Ti plasmid for mobilization. In like manner, any oncogenic strain of *A. tumefaciens* carrying a wild-type Ti plasmid with a functional vir region, which is capable of transferring its own Ti plasmid to a plant cell and transforming the plant cell, can be used in the present invention. Various strains of *Agrobacterium tumefaciens* that are suitable for use in the present invention are publicly available; see, e.g., ATCC Catalogue of Strain I, p.66 (15th edition, 1982).

A preferred embodiment of the invention utilizes a non-oncogenic, or avirulent, strain of *A. tumefaciens*. Such a strain can be constructed through the receipt of a Ti-plasmid from which the T-DNA region has been deleted. A particular strain of *Agrobacterium tumefaciens* available for use in the present invention is *A. tumefaciens* LBA-4404. The strain was developed by Dr. P. J. J. Hooykaas and is deposited in the Centrale Collectie van Schimmel-cultures (CBS) at Baarn as number CBS191.83. This strain is also deposited and made part of the Northern Regional Research Laboratory and is available to the public under the accession number NRRL B-15920. Plant cells exposed to this strain of bacteria do not form crown galls. Instead, hygromycin resistant callus is produced which is easily regenerated into mature plants.

The infection of plant tissue by Agrobacterium is a simple technique well known to those skilled in the art. Typically, a plant is wounded by any of a number of ways, which include cutting with a razor, puncturing with a needle, or rubbing with abrasive. The wound is then inoculated with a solution containing tumor-inducing bacteria. In the present invention, Agrobacteria containing a binary vector system consisting of the wild-type Ti plasmid and the micro-Ti plasmid pCEL44 were used to incite galls on aseptic decapitated seedlings of *Nicotiana tabacum* cv Wisconsin 38. In addition, a non-oncogenic strain of *A tumefaciens* containing the micro-Ti plasmid pCEL44 was used to induce callus production from leaf sections of *Nicotiana plumbaginifolia* and *Nicotiana tabacum* cv Wisconsin 38. Both of these varieties are readily available from the United States Department of Agriculture's Tobacco Research Laboratory, Box 16G, Oxford, N.C. 27565. The use of a cell from a specific type of plant is not critical to the present invention since a cell from any plant, into which a Ti plasmid can be transformed by Agrobacteria, can be utilized. For example, the cell can come from any dicotyledonous plant, such as, tomato, potato, tobacco, sunflower and soybean or from a monocotyledonous plant, such as members of the families, Liliaceae and Amaryllidaceae.

The resultant tumorous growths were excised and DNA was isolated from representative tobacco clones, digested with BamHI and BamHI plus HindIII restriction enzymes and Southern-blotted. The ~1.3 kb BamHI-BglII fragment conferring hygromycin resistance was nick-translated for use as a hybridization probe for analysis of the T-DNA structure.

A plant cell, transformed with a Ti plasmid in accordance with this invention, is used to regenerate a plant that expresses hygromycin resistance, as well as other functions, for which the Ti plasmid codes. The invention is useful for genetically modifying plant tissues and whole plants by introducing useful plant genes from other plant species or strains, such useful plant genes include, but are not limited to, genes coding for storage proteins, lectins, resistance factors against disease, insects and herbicides, factors providing tolerance to environmental stress and the like. The method, plasmids and transformants of the present invention provide plant breeders with a novel way of introducing desirable genes into plants, as well as to provide plant molecular biologists with molecular probes for studying plant development.

The examples, which follow, further illustrate this invention.

EXAMPLE 1

Culture of *E. Coli* RR1ΔM15/pCEL30 and Isolation of Plasmid pCEL30.

A. Culture of *E. coli* RR1ΔM15/pCEL30

*E. coli* RR1ΔM15/pCEL30 (NRRL B-15915) was grown in 750 ml of L medium (10 g/l caesin hydrolysate, 5 g/l yeast extract, 5 g/l NaCl, 1 g/l glucose, pH 7.4) containing ampicillin at 50 µg/ml according to conventional microbiological procedures. The culture was harvested after 24 hours incubation at 37° C. with vigorous shaking.

B. Isolation of Plasmid pCEL30

The culture was centrifuged and the cell pellet resuspended in 50 ml freshly-prepared lysis buffer (50 mM Tris-HCl pH 8, 10 mM EDTA, 9 mg/ml glucose, 2 mg/ml lysozyme). After 45 minutes incubation on the suspension was mixed with 100 ml of a solution that was 0.2N NaOH and 1% SDS and then kept on ice for a further 5 minutes. Another 90 ml of 3M sodium acetate was added and the mixture maintained on ice for 60 minutes.

Cell debris was removed by centrifugation and the supernatant was mixed with 500 ml ethanol. After 2 hours at −20° C., nucleic acid was pelleted by centrifugation and resuspended in 90 ml of 10 mM Tris-HCl pH 8, 10 mM EDTA.

The nucleic acid solution was mixed with 90 gm cesium chloride and 0.9 ml of a solution containing 10 mg/ml of ethidium bromide, then centrifuged at 40,000 rpm for 24 hours to purify the plasmid DNA. The plasmid DNA band was recovered and recentrifuged at 40,000 rpm for 16 hours. The plasmid DNA band was again recovered and freed of cesium chloride and ethidium bromide by conventional procedures and precipitated with 2 volumes of ethanol containing 90 g/l ammonium acetate. The pelleted DNA was dissolved in TE buffer (10 mM Tris-HCl pH 8, 1 mM EDTA) at a concentration of 0.2 mg/ml.

EXAMPLE 2

Culture of *Escherichia coli* JA221/pOW20 and Isolation of Plasmid pOW20

A. Culture of *E. coli* JA221/pOW20

This bacterium is grown as described for *E. coli* RR1ΔM15 in Example 1 above.

B. Isolation of Plasmid pOW20

This plasmid is prepared as described for plasmid pCEL30 in Example 1 above.

EXAMPLE 3

Construction of *Escherichia coli* RR1ΔM15/pCEL40

A. BglII Digestion of Plasmid pCEL30 and Treatment With Calf Intestinal Phosphatase Five µg of plasmid pCEL30 DNA were digested with 50 units of BglII restriction enzyme in a 150 µl reaction of the composition recommended by the enzyme manufacturer*. Digestion was allowed to proceed for 90 minutes at 37° C.

*Restriction and other enzymes can be readily obtained from the following sources:

Bethesda Research Laboratories, Inc.

Box 6010

Rockville, Md. 20850

Boehringer Mannheim Biochemicals

7941 Castleway Drive

P.O. Box 50816

Indianapolis, Ind. 46250

New England Bio Labs., Inc.

32 Tozer Road

Beverly, Mass. 01915

B. BamHI-BglII Digestion and Isolation of the ~1.3 kb Fragment of Plasmid pOW20

The reaction was first mixed with 8.75 µl of 0.5M Tris-HCl pH 8, 1 mM EDTA and then with 1.25 units of calf intestinal phosphatase (Boehringer Mannheim) and incubated at 37° C. for 15 minutes. The mixture was extracted with buffered phenol, then with ether and precipitated with 2 volumes of ethanol containing ammonium acetate. After 30 minutes at −70° C., the DNA was pelleted and redissolved in TE buffer at a concentration of 10 µg/ml.

About 20 µg of plasmid DNA is digested with the restriction enzymes BamHI and BglII according to the enzyme manufacturer's recommended procedures.

The DNA fragments resulting from this digestion are fractionated by conventional methods of agarose gel electrophoresis and isolated by entrapment on a piece of NA-45 DEAE paper (Schleicher & Schuell Inc., Keene, N.H. 03431) inserted into the gel during electrophoresis. DNA is eluted from the paper by spinning the paper for 5 seconds with a sufficient amount of a high salt buffer (1.0M NaCl; 0.1 mM EDTA; and 20 mM Tris, pH 8.0) to cover the paper in a micro-centrifuge. The paper is incubated at 55°–60° C. for 10–45 minutes with occasional swirling. The buffer is removed and the paper washed with about 50 µl of buffer. The DNA is extracted first with phenol and then with ether precipitated with two volumes of ethanol containing ammonium acetate, and resuspended in TE buffer at a concentration of about 25 µg/ml.

c. Ligation

Ten ng of the phosphatased, BglII-cut plasmid pCEL30 were mixed with 50 ng of the purified ~1.3 kb BamHI-BglII fragment in a 15 µl ligase buffer (50 mM Tris-HCl, pH 7.6; 10 mM MgCl$_2$; 10 mM DTT; and 1mM ATP) containing 0.8 units of T4 DNA ligase (BRL). The mixture was incubated overnight at 15° C.

D. Transformation of *E. coli* RR1ΔM15 and Selection

The ligation mixture was mixed with 15 µl sterile 60 mM CaCl solution. Next, 70 µl of a suspension of competent *E. coli* RR1ΔM15 cells, which had been stored 20 X concentrated in 30 mM CaCl, 15% glycerol at −70° C., were added. After 60 minutes on ice, the transformation mixture was heat-treated at 42° C. for 2 minutes and then incubated with 0.5 ml L medium for 90 minutes at 37° C.

Samples of mixture were spread on L medium containing ampicillin at 50 mg/l and solidified with agar at 15 g/l. These samples were then incubated overnight at 37° C. to permit growth of colonies from transformed cells.

E. Identification of Clones of *E. coli* RR1ΔM15 Containing Plasmid pCEL40

Colonies resulting from the transformation were inoculated into 5 ml L medium containing ampicillin at 50 mg/ml and grown overnight at 37° C. Plasmid DNA was prepared from 1 ml samples of these cultures by the procedure of Holmes & Quigley (*Analytical Biochemistry* 114:193; 1981) and redissolved in 50 µl of TE buffer.

The plasmids were digested in 10 µl reactions containing 7.5 µl of the DNA solution and about 5 units each of HindIII, PstI, BglII and BglII plus HindIII restriction enzymes and other reagents as suggested by the enzyme manufacturers. After 60 minutes at the appropriate temperature the digests were analysed by agarose gel electrophoresis using conventional procedures. The sizes of fragments produced from pCEL40 by restriction enzymes were consistent with the plasmid structure in FIG. 2.

EXAMPLE 4

Construction of Micro-Ti Plasmid pCEL44

A EcoRI Digestion of Plasmid pKT210 and Phosphatase Treatment

Five µg of plasmid pKT210 were digested with 50 units of EcoRI restriction enzyme in a 150 µl reaction of a composition recommended by the enzyme manufacturer. After 90 minutes of 37° C., the reaction was treated with calf intestinal phosphatase as described in Example 3 and dissolved in TE buffer at a concentration of 10 µg/ml.

EcoRI Digestion of Plasmid pCEL40

Fifteen µl of a preparation of plasmid pCEL40 DNA, constructed in Example 3E, were digested with 10 units of EcoRI restriction enzyme in a 20 µl reaction at 37° C. for 90 minutes and then extracted with phenol, followed by an ether extraction. The digested DNA was precipitated with 2 volumes of ethanol containing ammonium acetate at −20° C. and redissolved in 20 µl TE buffer.

C. Ligation, Transformation and Selection of *E. coli* RR1ΔM15/pCEL44

Ten ng of phosphatased, EcoRI-cut pKT210 were ligated with 5 µl of EcoRI-cut pCEL40 as described in Example 3C, and transformed into *E. coli* RR1ΔM15 as described in Example 3D.

Figure 3:
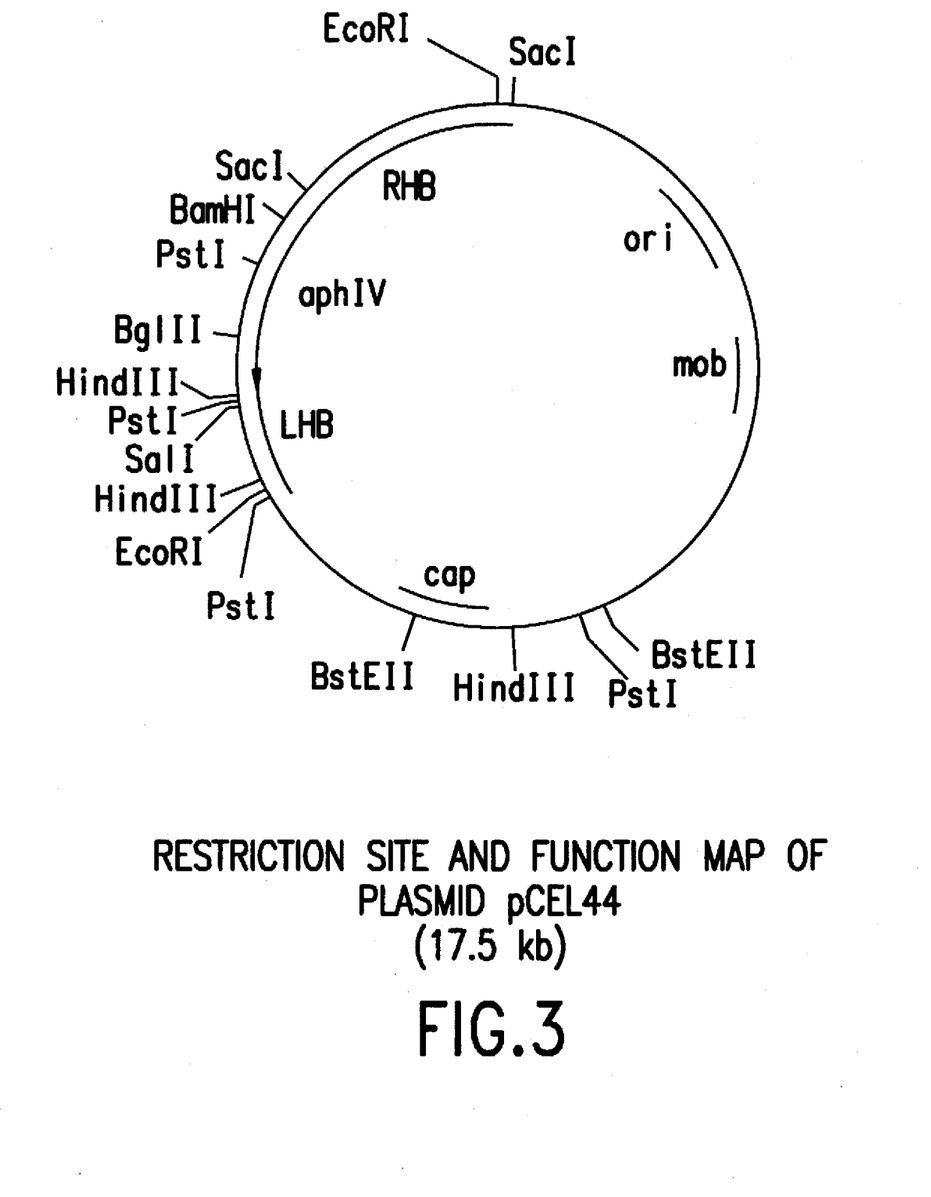
FIG. 3 shows the restriction site and function map of plasmid pCEL44.

Transformed cells were selected by their ability to grow on solidified L medium containing chloramphenicol at 10 mg/l Colonies containing pCEL44 were identified by PstI, HindIII and BamHI restriction enzyme analysis of their constituent plasmids as described in Example 3E. A restriction site and function map is presented in FIG. 3 of the accompanying drawings.

EXAMPLE 5

Conjugation of pCEL44 Into *Agrobacterium tumefaciens* LBA4013

A. Growth of Parental Strains

*Escherichia coli* K12 RR1ΔM15/pCEL44 and *E. coli* pRK2013 were grown overnight at 37° C. on solidified L medium. *Agrobacterium tumefaciens* LBA4013 was grown for 2 days at 28° C. on solidified L medium.

B. Triparental Conjugation and Selection

One loop of each of the three strains described above were mixed in 1 ml of 30 mM magnesium sulfate solution. Next, a drop of the mixture was placed on solidified TY medium (5 g/l caesin hydrolysate, 5 g/l yeast extract, 15 g/l agar) and incubated at 28° C. overnight.

The bacterial growth was resuspended in 3 ml of 10 mM magnesium sulfate solution and 0.1 ml samples of serial dilutions were spread on solidified TY medium containing 100 mg/l nalidixic acid and 2 mg/l chloram-phenicol and incubated at 28° C.

Transconjugants gave rise to individual colonies after 2 to 4 days growth. These were inoculated singly into 25 ml liquid TY medium containing 100 mg/l nalidixic acid and 2 mg/l chloramphenicol and incubated at 28° C. with shaking for another 2 days. The plasmid content of the transconjugants was then checked by the method of Casse et al. (*Journal of General Microbiology* 113:229–242; 1979).

EXAMPLE 6

Introduction and Expression of Hygromycin Resistance in Tobacco Crown Gall Cells Aseptic tobacco plants of cultivar Wisconsin 38 were raised as follows. Seed was sterilized by a 10 minute treatment with 10% Clorox bleach, followed by a rinse with 95% ethanol and then extensive rinsing with sterile water. Seed was planted on the surface of medium R5, which consists of MS major and minor salts (*Physiol. Plant.* 15:473–497, 1962), with 30 g/l sucrose, 100 mg/l myo-inositol (Sigma), 2.5 mg/l thiamine HCl (Eli Lilly and Company), 2.5 mg/l nicotinic acid (Matheson Coleman Bell), 1.25 mg/l pyridoxine HCl (Lilly), and 1.25 mg/l Ca pantothenate (Sigma), pH 6, solidified with 9 g/l Difco Bacto agar. Germinated seeds were picked onto the same R5 medium and the plants were maintained by making vegtative cuttings approximately every 2 months into Magenta GA7 boxes. They were grown in a lighted incubator with a day length of 16 hours, light intensity of about 150 lux, and a temperature of 26° C.

To inoculate with Agrobacterium, the sterile plants were decapitated and defoliated with a sterile scalpel, leaving a large wound at the apex and the cut petioles extended. Within a few minutes, a culture of *Agrobacteria tumefaciens* LBA 4013/pCEL44 was applied to cut surfaces until a cream-brownish accumulation was visible to the naked eye. The inoculated, wounded plants were labeled, sealed in boxes, and placed back into the lighted incubator. Care was taken to insure that ambient temperature was never over 30° C. during gall induction.

Fifteen days after inoculation, visible galls had grown out of most wound inoculation sites on the sterile Wisconsin 38 plants. These galls were cut off individually, numbered, and placed onto R5 medium which had been supplemented with 200 µg/ml each carbenicillin (Sigma) and vancomycin (Vancocin HCl Lilly). This treatment, intended to kill the tumor-inciting bacteria and give aseptic cultures, involved culturing the crown galls in the dark at 25° C. to 27° C. for three weeks on the above antibiotics, followed by another three-week passage on those antibiotics.

To test the response to hygromycin of these crown gall callus tissue cultures, 100 mg callus samples were placed onto Falcon 1007 petri dishes filled with about 15 ml of callus growth medium containing MS salts, 30 g/l sucrose, 1 mg/l thiamine HCl, 100 mg/l myo-inositol, 9 g/l Difco Bacto-agar, 1 mg/l IAA (indole-3-acetic acid, Sigma), 0.1 mg/l kinetin (6-furfurylaminopurine, Sigma), pH 6. After these samples were sterilized, the aforementioned concentrations of vancomycin and carbenicillin, and 50 µg/ml of hygromycin B (Lilly) were added. This test was read after three weeks of incubation in the dark at 27° C. and positive growth phenotypes recovered.

EXAMPLE 7

Presence of aphIV Sequences in Hygromycin-Resistant Gall Tissues

A. Southern Blot of Plant DNA

Nuclear DNA was prepared from about 10 gm of gall tissue by the method of Rivin et al. described in "Maize for Biological Research" pp. 161–164 (ed W. F. Sheridan, publ. Plant Molecular Biology Assn; Charlottesville, Va., 1982).

Ten µg of each DNA was digested with 100 units each of BamHI and BamHI plus HindIII restriction enzymes in a 200 µl reaction of the composition recommended by the enzyme manufacturer. After 4 h incubation at 37° C., the digested DNA was precipitated with 400 µl of ethanol containing ammonium acetate for 30 minutes at −70° C. The DNA was allowed to dissolve overnight at 4° C. in 25 µl of TE buffer.

The digested DNA fragments were fractionated by conventional agarose gel electrophoresis and transferred to GeneScreen, a hybridization transfer membrane (New England Nuclear, Boston, Mass. using the manufacturer's protocol.

B. Probe from the 1.3 kb Fragment of Plasmid pOW20

A hybridization probe is made from the fragment of plasmid pOW20 purified as in Example 3B. The fragment is nick-translated by conventional procedures (see Maniatis et al., 1982 Molecular Cloning, Cold Spring Harbor Laboratory, Cold Spring Harbor, N.Y.) using DNase I and DNA polymerase such that the probe contains about 20 µCi of [32-P]dCTP per 0.2 µg of DNA.

C. Hybridization to Detect aphIV Sequence Homology

GeneScreen containing plant DNA fragments was prehybridized overnight at 42° C. in a solution containing 0.75 M NaCl, 75 mM sodium citrate, 25 mM sodium phosphate pH 6.7, 2 g/l Ficoll 400, 2 g/l polyvinylpyrrolidone 360, 2 g/l bovine serum albumen, 1% sodium dodecyl sulfate, 10% dextran sulfate, 50% formamide and 250 mg/l denatured, sonicated calf thymus DNA.

Hybridization was in fresh solution of the same composition but supplemented with heat-denatured probe DNA (0.2 µg per 25 ml of solution). After overnight incubation at 42° C., the GeneScreen membrane was washed twice with GS buffer (0.3 M NaCl, 60 mM Tris-HCl, 2 mM EDTA, pH 8). Each wash was performed for 1 hour at room temperature. The membrane was then washed stringently with 0.1 X GS buffer supplemented with 1% SDS for 1 hour at 70° C. This step was repeated and then the GeneScreen was washed twice more at room temperature with 0.1 X GS buffer. The membrane was blotted dry and exposed to X-ray film overnight at −70° C. with intensifying screens.

EXAMPLE 8

Regeneration of Plants

A. Regeneration from Uncloned Gall Tissue

Uncloned gall tissue which had demonstrated strong growth in the presence of a restrictive level of hygromycin B was subjected to a treatment intended to induce plant regeneration under selective pressure. This treatment comprised placing pieces of callus tissue on MS medium with 0.3 mg/l IAA and 10 mg/l 2-ip (6-gamma, gamma-dimethylallyl aminopurine, Gibco*) 100 mg/1 myoinositol, 1 mg/l thiamine HCl, pH 6, 30 g/l sucrose, solidified with 0.9% Difco Bacto-agar plus 50 µg/ml of hygromycin. These preparations were placed in a lighted incubator for one month and then dark green and budding areas of tissue were selected and transferred to the same high-cytokinin, hygromycin-supplemented medium again for another month of incubation in the light. Following these two passages on regeneration medium plus antibiotic, any green, budding clumps of plantlets were cut to excise single plants which were further cultured on solid medium R5 for sterile plant growth in the light. When well-developed plants were obtained from three different tissue lines, the expression of the hygromycin resistance gene in these plants was tested as follows. Leaf pieces about a cm square were cut out and placed onto callus growth medium with or without hygromycin.

* Plant media and supplements can be readily obtained from Gibco, Grand Island, N.Y.

Control tissues were leaf pieces from the aseptic Wisconsin 38 plants which were starting material for these crown gall induction experiments. These preparations were incubated in the dark at 27° C. After three weeks, the Wisconsin 38 and the regenerated gall tissue plants both showed leaf cell enlargement and callus growth at the edges of the leaf piece explants in antibiotic-free medium. In the antibiotic-containing medium, however, the control Wisconsin 38 leaf material was unable to initiate cell division and was brown and dying, while the leaves from plants regenerated under selection pressure from hygromycin-resistant gall cultures showed a cell expansion, growth and callus production comparable to the no-hygromycin dishes. These results indicate that the regenerated plants contain and are capable of expressing the hygromycin resistance gene from pCEL44.

B. Single Cell-Derived Clones from Hygromycin Resistant Galls

Hygromycin-resistant crown gall lines were maintained in the dark at 27° C. without antibiotics, with monthly subcultures on medium 1/.1 (MS salts with 1 mg/l IAA and 0.1 mg/1 kinetin, 0.9 g/l Difco Bacto agar, 100 mg/l myoinositol, 1 mg/l thiamine HCl, 30 g/l sucrose, pH 6, autoclaved to sterilize and dispensed 50 ml/dish into Falcon 1005 petri dishes). Samples from these culture lines were dispersed into the same medium, which had been prepared without agar and dispensed 50 ml/flask in 125-ml erlenmeyer flasks and plugged with Jaece foam stoppers. Suspension cultures initiated in this way were shaken at 135 rpm in a gyrotory shaker in the dark at 27° C. After a week, the hard clumps of callus were removed and the suspension cultures of crown gall cells were passaged by dividing 1:1 into fresh liquid medium on a weekly basis. These short-term suspensions can also be cultured for a month before reverting to callus clumps in the shake cultures.

To generate single-cell-derived clones, protoplasts were prepared from these cultures and then cultivated at extremely low population density, as follows. The short-term suspension cultures were centrifuged lightly to concentrate the cells; the growth medium in the supernatant was removed, and 5 ml packed cell volume of the cells was mixed with 25 ml of a filter-sterilized enzyme mixture consisting of 6% w/v cellulysin (Onozuka R10, Kinki Yakult Mfg., Japan), 1% w/v macerase (Macerozyme R10, also from Kinki Yakult), 9% w/v mannitol (Sigma), 3 mM MES (2-(N-morpholine)-ethane sulfonic acid, Sigma), pH 5.8. The cell plus enzyme mixture was placed in a Falcon 1005 petri dish and incubated 4½ hours at room temperature with slow rotary shaking at 50 rpm. When microscopic observation showed protoplast release, this preparation was filtered through wire mesh screens of aperture size 259 and 231 microns (W.S. Tyler, Inc. of Mentor, Ohio), and mixed 1:1 with protoplast culture medium which had been made up to 25% w/v Ficoll DL (Sigma). This mixture was placed in the bottom of a round-bottom glass centrifuge tube and overlayered with a few ml of the same protoplast culture medium made up to 8% w/v Ficoll, and finally, with a thin 1–2 ml layer of the protoplast culture medium made up to 2% w/v Ficoll. All Ficoll-containing solutions had been filter-sterilized. These discontinuous density gradient preparations were capped and centrifuged in a swinging bucket, ambient-temperature centrifuge at 50×G for 30 minutes. The protoplasts were layered at the top and collected with a wide-bore pasteur pipet at high population density, $2 \times 10^5$ viable cells per ml in this experiment. The protoplast culture medium used was KP (medium K3 of Kao & Michayluk, Planta 120:215–227, 1974, as modified by Caboche in Muller et al., Physiol. Plant. 57:35–41, 1983), made up to an osmotic strength of 0.5M with mannitol.

Protoplasts thus collected were cultured at the high population density (as collected), in aliquots of 1 ml in Falcon 3001 dishes, in the dark at 26° C. After six days, they were examined for growth, cell viability as determined by exclusion of the vital stain Evans blue (Sigma), and cell wall formation and divisions. Their diameter was measured under the microscope. The preparation was filtered through a 107 microns diameter wire mesh filter. The preparation was checked for the absence of cell aggregates. The cells then were serially diluted, with population density counting, to a final population density of about 100 viable cells per ml in medium C of Caboche, supra which had been adjusted to the same osmotic strength as the culture medium, using mannitol. About 15 ml per dish were plated and placed in the lighted incubator. Single-cell-derived colonies were obtained in a month with some cultures, and after two months with other cultures. These colonies were picked from the liquid medium with a wide-bore pasteur pipet and placed on a Whatman #3 filter paper soaked in liquid medium 1/0.1. These paper-supported cultures were continued in the light for another month with additions of the liquid medium to the paper when needed, followed by picking onto solid medium 1/0.1 and cultured in the dark at 27° C.

In a test for the expression of hygromycin resistance in single cell-derived callus cultures, paired samples of cloned lines of callus tissue were plated on solid medium 1/0.1 with 50 µg/ml hygromycin B, and on the same medium without antibiotic. After 3 weeks of culture in the dark at 27° C., the two dishes were compared. In 52 out of 56 cases, the calli exhibited hygromycin resistance by growing as well with the 50 µg/ml hygromycin B as without.

C. Regeneration from Cloned Tissue

The hygromycin-resistant callus tissue cultures derived from the protoplast method of single cell cloning in section 8B can be subjected to a regenerating protocol. Callus pieces are placed on solid medium containing MS salts, 100 mg/l myo-inositol, 1 mg/l thiamine HCl, 0.3 mg/l IAA, 10 mg/l 2-ip, 0.9 g/l Difco Bacto-agar, 30 g/l sucrose, pH 6 and cultured in the light for one month. Green and budding pieces of tissue are passaged again on the same medium. Plantlets formed under this regime are passaged onto medium R5, described in section 6 above, for development into well-formed plants in the light. The plants obtained are tested for the expression of the hygromycin resistance gene from plasmid pCEL44 by incubating leaf piece explants in the dark on callus growth medium containing hygromycin, as described in section 8A above. The plants demonstrate expression of the hygromycin resistance gene by showing leaf cell expansion and callus formation on the cut edges of the leaf piece explants, as in section 8A.

These plants are transplanted into soil and brought to sexual maturity in the greenhouse so that Mendelian inheritance of the hygromycin resistance gene is demonstrated. This proves that the binary vector containing pCEL44 can transfer only the hygromycin resistance gene without the tumor-inducing oncogenes, providing a new and useful way to engineer desired traits into plant cells which can be regenerated into sexually competent plants.

EXAMPLE 9

Conjugation of pCEL44 into Agrobacterium tumefaciens LBA4404

A triparental cross between E coli K12 RR1ΔM15, E. coli pRK2013 and A. tumefaciens LBA4404 (NRRL B-15920) was performed as described in Example 5. Transconjugants were selected on solidified TY medium containing 20 mg/l rifampicin and 2 mg/l chloramphenicol.

EXAMPLE 10

Introduction and Expression of Hygromycin Resistance in Callus

A. Nicotiana plumbaginifolia

Seeds of N. Plumbaginifolia were sterilized by a brief exposure to ethanol followed by a 3 minute treatment with 0.5% Chlorox bleach. After rinsing with sterile water the seeds were incubated for 1 hour in a solution containing 0.5 mg/ml gibberillic acid. Next, the seeds were planted on MS medium solidified with 0.6% Phytagar. Plants were grown at 27° C. with a daylength of 16 hours at a light intensity of about 700 lux.

Leaf sections of about 1 sq cm were cut from 3 month-old plants and the cut edges were smeared with a culture of Agrobacterium tumefaciens LBA4404/pCEL44. The infected sections were incubated on solidified MS medium containing 1 mg/l napthaleneacetic acid (NAA) and 0.1 mg/l benzyladenine (BA) for 3 days in the dark at 27° C. The sections were then transferred to the same medium supplemented with 200 mg/l vancomycin and 200 mg/l carbenicillin. After growth for one month, pieces of callus were transferred to MS medium with 1 mg/ml NAA, 0.1 mg/ml BA and 50 mg/l hygromycin B and the incubation continued.

After 3 weeks, small pieces of callus were inoculated onto solidified MS medium supplemented with 0.1 mg/l NAA and 1 mg/l BA and incubated at 27° C. in the light with a 16 hour day to regenerate shoots. The shoots are transferred to solidified MS medium without supplements to promote root growth.

B. Nicotiana tabacum

A portion of a tobacco callus suspension culture, NT575, was poured onto solid media (described in Example 8C). After excess water was removed, a feeder layer system was constructed wherein two layers of sterilized Whatman #1 filter paper were placed over the cells. The cells were incubated in the dark at 26° C. overnight.

A culture of Agrobacterium tumefaciens LBA-404/pCEL44 was grown up on TY media with 2 mg/l chloramphenicol. Isolates were transferred into a liquid medium containing 5 g/l casein hydrolysate and 3 g/l yeast extract, and shaken overnight at 26° C. in a gyrotory shaker. Leaf sections of about 1 sq cm were cut from 3 month-old plants and soaked in the liquid overnight bacterial culture for 6–8 minutes, blotted dry and placed onto the filter paper cover of the above prepared feeder layer system.

The leaf pieces were incubated in the light at 26° C. for two days, and then picked off and placed on regeneration medium plus 200 µg/ml each carbenicillin and vancomycin. After an additional 12 days in the light on this medium, the leaf pieces were moved onto the same medium with 50 µg/ml hygromycin. These plates were cultured in the light of 26° C. for an additional 3 months.

Plantlets were regenerated and grew out on the hygromycin-containing medium from the treated leaf pieces. Pieces which had been treated in the same way but with Agrobacteria containing the hygromycin resistance gene in an inverted orientation gave no plantlets.

Plants are picked from these leaf sections, grown in hormone-free R5 medium and tested for hygromycin resistance by explanting leaf pieces onto callus growth medium containing 50 µg/ml hygromycin B in substantial accordance with the teaching of Example 8A.

Similarly, leaf sections are treated as taught above, except that callus growth medium (Example 10A) is used in place of the regeneration medium. These leaf sections are grown in callus growth medium supplemented with 200 µg/ml each vancomycin and carbenicillin. These preparations are incubated in the dark at 26° C. for 2 weeks and then moved to the supplemental medium containing 50 µg/ml hygromycin B. Hygromycin resistance is proven by growing callus on antibiotic-containing media and by probing Southern blots of the plant DNA with the aphIV sequence as taught in Example 7.

I claim:

1. A chimeric gene functional in a plant cell, which chimeric gene comprises:

(a) at a position 5' to coding region (c), a plant-expressible promoter sequence;

(b) at a position 3' to coding region (c), a terminator signal sequence; and (c) a coding region of an aphIV gene, which coding region: (i) encodes a functional hygromycin phosphotransferase enzyme; and (ii) is positioned between such plant-expressible promoter sequence (a) and such terminator signal sequence (b) so as to be expressible, wherein expression of such coding region in a plant cell confers resistance to hygromycin B on such plant cell and wherein such resistance to hygromycin B is capable of providing a basis for selection of such plant cell.

2. The gene of claim 1 wherein, in the 3' direction from the promoter sequence, and before the 5' end of the coding region there is an amino terminal region-encoding sequence, which amino terminal region-encoding sequence is under transcriptional control of said promoter sequence when the promoter sequence is naturally occurring.

3. The gene of claim 1 wherein the promoter sequence is from an octopine synthetase gene.

4. The gene of claim 2 wherein the amino terminal region-encoding sequence is from an octopine synthetase gene.

5. The gene of claim 1 wherein the terminator signal sequence is a nopaline synthetase terminator signal sequence.

6. The gene of claim 1 wherein the promoter sequence is from an octopine synthetase gene and the terminator signal sequence is a nopaline synthetase terminator signal sequence.

7. The gene of claim 2 wherein the amino terminal region-encoding sequence codes for messenger RNA, which messenger RNA comprises a start codon.

8. The gene of claim 7 wherein the amino terminal region-encoding sequence codes for the first eleven amino acids of the octopine synthetase gene.

9. The gene of claim 1 wherein the coding region, the expression of which coding region confers resistance to hygromycin B, is derived from the ~1.3 kb BamHI-BglII restriction fragment of plasmid pOW20, which plasmid pOW20 is obtainable from NRRL B-15838.

10. A recombinant DNA plant expression vector comprising (a) the chimeric gene of any of claims 1–9; and (b) a DNA fragment containing a replicon, which replicon is functional in an Agrobacterium.

11. A recombinant DNA plant expression vector comprising (a) the chimeric gene of claim 9; and (b) a DNA fragment containing a replicon functional in an Agrobacterium, which DNA fragment is derived from the ~11.8 kb EcoRI fragment of plasmid pKT210.

12. The vector of claim 11 which is a plasmid.

13. The vector of claim 12 which is a micro-Ti plasmid.

14. The vector of claim 13 which is plasmid pCEL44.

15. Plasmid pCEL40 shown in FIG. 2 and derivable by ligating the BglII digest of plasmid pCEL30, to the ~1.3 kb BamHI-BglII fragment of plasmid pOW20, such plasmids pCEL30 and pOW20 being obtainable from NRRL B-15915 and NRRL B-15838, respectively.

16. A method for selecting a hygromycin B-resistant recombinant DNA-containing plant cell from a population of hygromycin B-sensitive plant cells, which method comprises (a) inserting the chimeric gene of claim 1 into a hygromycin B-sensitive plant cell within such population of hygromycin B-sensitive plant cells and (b) selecting a hygromycin B-resistant plant cell which expresses such inserted chimeric gene by exposing such cell and such population of hygromycin B-sensitive plant cells to an amount of hygromycin B sufficient to prevent the growth of such population of hygromycin B-sensitive plant cells but which permits the growth of such hygromycin B-resistant plant cell, and allowing such hygromycin B-resistant plant cell to grow.

17. The method according to claim 16, in which the hygromycin B-resistant recombinant DNA-containing plant cell is a dicotyledonous hygromycin B-resistant recombinant DNA-containing plant cell and the population of hygromycin B-sensitive plant cells is a population of dicotyledonous hygromycin B-sensitive plant cells.

18. The method of claim 17 wherein the insertion of the chimeric gene is mediated by an *Agrobacterium tumefaciens* strain, which strain has been transformed with a vector comprising such chimeric gene.

19. A method for regenerating mature dicotyledonous plants from selected hygromycin B-resistant dicotyledonous plant cells, which method comprises (a) inserting the chimeric gene of claim 1 into a hygromycin B-sensitive dicotyledonous plant cell, (b) selecting a dicotyledonous plant cell expressing hygromycin B-resistance by exposing such cell to an amount of hygromycin B sufficient to prevent the growth of such cell were such cell not hygromycin B-resistant, and permitting such hygromycin B-resistant cell to grow, (c) culturing the selected hygromycin B-resistant dicotyledonous plant cell under conditions suitable for regeneration of a mature dicotyledonous plant, and (d) regenerating a mature dicotyledonous plant.

20. A plant cell containing recombinant DNA comprising the chimeric gene of any of claims 1–9.

21. The plant cell of claim 20 which is a dicotyledonous plant cell.

22. A transgenic, hygromycin B-resistant dicotyledonous plant comprising the dicotyledonous plant cell of claim 21, or hygromycin B-resistant progeny thereof.

23. A plant part from the plant of claim.

24. A seed from the plant of claim 22.

25. The method according to claim 16 in which the hygromycin B-resistant recombinant DNA-containing plant cell is a monocotyledonous hygromycin B-resistant recombinant DNA-containing plant cell and the population of hygromycin B-sensitive plant cells is a population of monocotyledonous hygromycin B-sensitive plant cells.

26. The plant cell of claim 20 which is a monocotyledonous plant cell.

27. A plant cell culture comprising the plant cell of claim 20.

* * * * *